us

United States Patent [19]

Tsukagoshi et al.

[11] Patent Number: 5,632,895
[45] Date of Patent: May 27, 1997

[54] SERUM SEPARATING DEVICE AND APPARATUS FOR SERUM SEPARATION

[75] Inventors: Youichi Tsukagoshi, Tokyo; Toshimasa Yamamoto, Kawasaki, both of Japan

[73] Assignee: Nigata Engineering Co., Ltd., Tokyo, Japan

[21] Appl. No.: 288,997

[22] Filed: Aug. 11, 1994

[30] Foreign Application Priority Data

Aug. 13, 1993 [JP] Japan ............................... 5-201664
Nov. 10, 1993 [JP] Japan ............................... 5-281519

[51] Int. Cl.⁶ .......................... B01D 21/26; B01D 17/038
[52] U.S. Cl. ........................ 210/518; 210/516; 210/789
[58] Field of Search .............................. 210/516, 518, 210/782, 789; 422/101

[56] References Cited

U.S. PATENT DOCUMENTS

| 1,859,362 | 5/1932  | Grauman et al. | 210/514 |
|-----------|---------|----------------|---------|
| 3,814,248 | 6/1974  | Lawhead        | 210/117 |
| 3,897,343 | 7/1975  | Ayres          | 210/516 |
| 3,920,557 | 11/1975 | Ayres          | 210/516 |
| 4,055,501 | 10/1977 | Cornell        | 210/516 |
| 4,083,788 | 4/1978  | Ferrara        | 210/516 |
| 4,088,582 | 5/1978  | Murty et al.   | 210/516 |
| 4,189,385 | 2/1980  | Greenspan      | 210/518 |
| 4,294,707 | 10/1981 | Ikeda et al.   | 210/516 |
| 4,464,254 | 8/1984  | Dojki et al.   | 210/516 |
| 5,266,199 | 11/1993 | Tsukagoshi et al. | |

FOREIGN PATENT DOCUMENTS

| 0 017 127 | 10/1980 | European Pat. Off. . |
| 0 040 022 | 11/1981 | European Pat. Off. . |
| 0 055 234 | 6/1982  | European Pat. Off. . |
| 51-105890 | 7/1975  | Japan . |

*Primary Examiner*—John Kim
*Attorney, Agent, or Firm*—Hoffmann & Baron

[57] ABSTRACT

The present invention provides a serum separating device and an apparatus for use in serum separation which is capable of completely separating serum and clot during the separation of a blood sample into serum and clot by means of a centrifugal separation operation. The serum separating device in accordance with the present invention is provided with a cylindrical member, which fits to an opening of a blood collection tube and which has an inner diameter which is slightly smaller than an inner diameter of the opening, and a movable member, the movable member comprising: a member main portion which is inserted into the cylindrical member and which presses against inner walls of the cylindrical member, and an annular isolating member which fits to an outer circumferential portion of the member main portion; wherein: the movable member has a specific gravity between that of serum and that of clot; and the annular isolating member comprises at least one of a material possessing elasticity and liquid permeability, and a material possessing the quality of swelling in response to immersion in liquid.

23 Claims, 5 Drawing Sheets

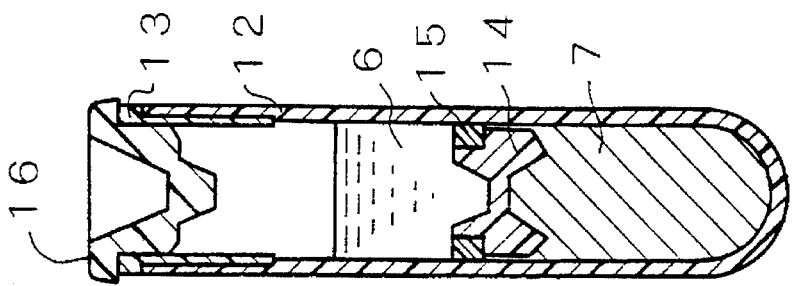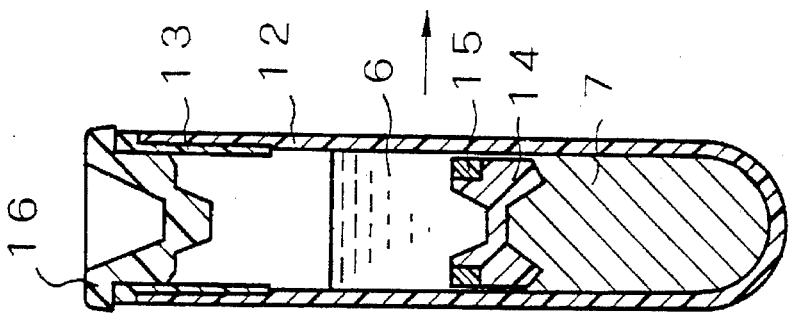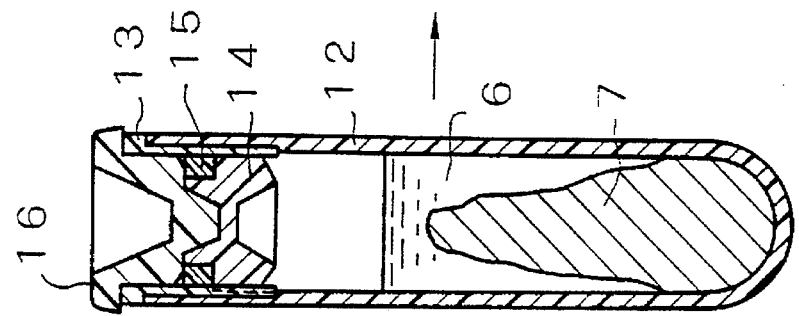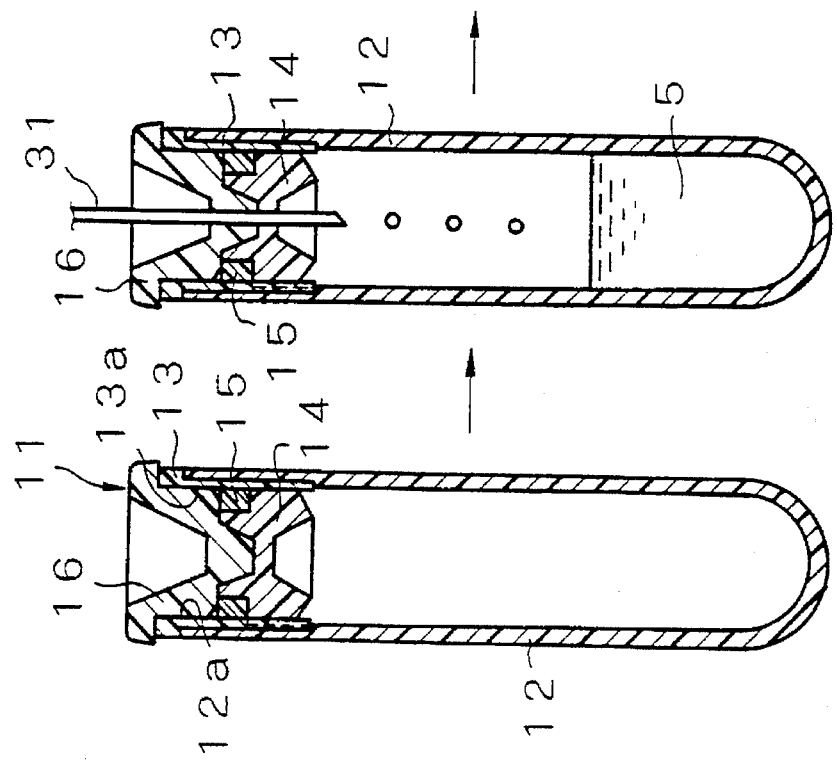

SERUM SEPARATING DEVICE AND APPARATUS FOR SERUM SEPARATION

BACKGROUND OF THE INVENTION

The present invention relates to a serum separating device and an apparatus for serum separation which are used at the time of the separation of a blood sample into serum and clot by means of centrifugal separation and the like.

Conventionally, since diagnostic tests for blood samples are primarily conducted using serum (plasma), a preprocessing operation prior to testing is required in which a blood sample which is collected in a blood collection tube is separated into a serum or plasma (hereinafter referred to as serum) and a clot or blood cells (hereinafter referred to as a clot).

Commonly, in such a serum separation operation, the whole blood sample which is collected is placed in a blood collection tube, this is subjected to centrifugal separation, and the serum which comprises the sample is separated therefrom. However, in such centrifugal separators, the state of the separation of the serum and the clot is extremely unstable, and if the slightest shock is applied, the blood cells present in the clot which is sedimented contaminates the serum, so that extremely careful operations are required in the handling of the blood sample after separation.

Various devices have been proposed in order to improve this unstable separation state of the blood sample after centrifugal separation, and to simplify the testing operation; an example thereof is a method employing a sealant possessing thixotropic characteristics and having a specific gravity between that of serum and clot.

This sealant has, for example, a synthetic resin of low molecular weight such as silicone oil or the like as a primary component thereof, and possesses a stable specific gravity and thixotropic characteristics; during centrifugal separation, this sealant becomes liquid and forms a strong partition above the clot.

However, the following difficulties are present in this sealant.

(1) In the case in which the material in the clot is abnormal, it is impossible to form a strong partition. For example, in the case in which the specific gravity of the clot is small and the clot is soft, as is seen in dialysis patients, it is impossible to completely separate the serum from the clot.

(2) Since the sealant is water insoluble, the sealant is mutually dissolvable with lipid-soluble drugs which are difficult to dissolve in water. Accordingly, in the case in which the drug concentration present in the blood is to be measured, there are cases in which the drugs dissolve in the sealant, and the values obtained by diagnostic tests are thus incorrect.

(3) In the case in which blood coagulation factor is the object of test, the sealant activates the blood coagulation factor, so that it is impossible to employ such a sealant.

(4) Blood properties vary from person to person. In particular, the generation of fibrin is a hindrance to the diagnostic test of serum after centrifugal separation, so that it is necessary to screen this fibrin which is thus generated; however, when a sealant is employed, it is impossible to screen this fibrin. Fibrin is particularly readily generated in the blood of dialysis patients, so that it is impossible to prevent the generation of fibrin when a sealant is employed.

The use of, for example, a serum filtering piston such as that shown in FIG. 9 is proposed to solve these difficulties with the use of the sealant (Japanese Patent Application, First Publication, Laid-Open No. Sho 51-105890).

This serum filtering piston 1 comprising a disc-shaped filter 2 with a diameter which slightly larger than the inner diameter of the blood collection tube, and a cylindrical weight 3 which attaches to the center of filter 2 and a diameter which smaller than that of filter 2; as shown in FIG. 10, after the collected blood 5 is placed in the blood collection tube 4, the serum filtering piston 1 is inserted into the blood collection tube 4, and by means of subsequently conducting centrifugal separation, as shown in FIG. 11, this serum filtering piston 1 moves to the boundary between serum 6 and clot 7, and since the filter 2 is in tight contact with the inner wall 4a of the blood collection tube 4, serum 6 and clot 7 are completely separated, and it is possible to obtain the serum by means of decanting.

An evacuated blood collection tube, in which a rubber stopper is inserted in an evacuated state into the mouth of a conventional blood collection tube, is employed as the vessel used in serum separation; however, recently, the use of an evacuated blood collection tube, in which a gas-barrier-type film such as aluminum laminate or the like is heat-sealed onto the mouth of a blood collection tube in an evacuated state, and a thin rubber flap is attached to the center of this film, has been proposed in order to increase air-tightness.

However, the serum filtering piston 1 described above has a construction in which the filter 2 is fastened to the weight 3 by a pin, so that there is some danger that the filter 2 will be torn off. Furthermore, in piston 1, filter 2 is drawn downward in a sliding manner, so that it is necessary that filter 2 possess a certain degree of strength, so that it bends and moves downward while sliding along the inner wall 4a of the blood collection tube 4. For this reason, the clot which adheres to the inner wall 4a is scraped, and this leads to blood cell breakage, so that as an effect thereof, inaccurate test values of LDH (lactic acid dehydrogenase) or the like occur. Furthermore, filter 2 moves easily from side to side, so that accordingly, it is difficult to continuously support the filter 2 horizontally in a balanced manner, and there are problems in that during the recovery of serum after centrifugal separation, the blood cells present in clot 7 pass through the gap between the inner wall 4a of blood collection tube 4 and filter 2 and contaminate serum 6, and the clot becomes attached above filter 2.

An attempt has been made to employ a rubber sheet possessing elasticity in place of the serum filtering piston 1; however, because the resistance of the rubber sheet to sliding is large, it is difficult to move this sheet smoothly down the inner wall of the blood collection tube, and in particular, in the case in which there is a variation in the inner diameter of the blood collection tube such that the diameter becomes smaller toward the bottom of the tube, as is the case in plastic blood collection tubes, it is extremely difficult to move the rubber sheet downwards in a smooth manner, and there is a problem in that it is difficult to completely separate the serum and the clot.

Furthermore, in evacuated blood collection tubes employing rubber stoppers such as those described above, there are problems in that in order to maintain air-tightness, the surface area of the blood collection tube and rubber stopper which are in contact is enlarged, and it is necessary to force this rubber stopper into the tube in a considerably forceful manner, and the rubber stopper itself becomes large, and furthermore, it is not easy to remove the rubber stopper. Furthermore, when a rubber stopper is employed, there is a problem in that it is impossible to prevent the occurrence of the so-called "pop-up" phenomenon. What is meant by the "pop-up" phenomenon is a phenomenon which occurs when the stopper has been removed from the vessel and is then reinserted; as a result of the reinsertion of the stopper, the air within the vessel is compressed, and as a result of the expansion of this compressed air, the stopper comes out.

Furthermore, when an evacuated blood collection tube is employed onto which a gas-barrier-type film is heat-sealed, when centrifugal separation is completed and the serum is to be moved to another vessel, the time-consuming removal of the film must be performed by hand.

SUMMARY OF THE INVENTION

The present invention has as an object thereof to provide a serum separating device and an apparatus for use in serum separation which are capable, when separating serum and clot of a blood sample by means of centrifugal separation, of completely separating serum and clot.

A first aspect of a serum separating device in accordance with the present invention is provided with: a cylindrical member, which fits to an opening of a blood collection tube and which has an inner diameter which is slightly smaller than an inner diameter of the opening; and a movable member, the movable member comprising: a member main portion which is inserted into the cylindrical member and which presses against inner walls of the cylindrical member, and an annular isolating member which fits to an outer circumferential portion of the member main portion; wherein: the movable member has a specific gravity between that of serum and that of clot; and the annular isolating member comprises at least one of a material possessing elasticity and liquid permeability, and a material possessing the quality of swelling in response to immersion in liquid.

In accordance with the serum separating device having the composition described above, it is possible to affix the member main portion at a predetermined position, and to completely separate the serum and the clot by means of this serum separating device, so that there is no danger that blood cells present in the clot will contaminate the serum. Furthermore, even in cases in which there is some variation in the inner diameter of the blood collection tube, it is possible to completely separate the serum and the clot.

An apparatus for serum separation in accordance with the second aspect of the present invention is provided with: a cylindrical blood collection tube having an opening at one end thereof; a cylindrical member which fits to the opening of the blood collection tube and which has an inner diameter which is slightly smaller than the inner diameter of the opening; and a movable member, the movable member comprising: a member main portion which is inserted into the cylindrical member and which presses against inner walls of the cylindrical member, and an annular isolating member which fits to an outer circumferential portion of the member main portion; wherein: the movable member has a specific gravity between that of serum and that of clot; and the annular isolating member comprises at least one of a material possessing elasticity and liquid permeability, and a material possessing the quality of swelling in response to immersion in liquid.

An apparatus for use in serum separation in accordance with the third aspect of the present invention is provided with: a blood collection tube formed with a reduced-diameter portion having a reduced inner diameter at an opening of the blood collection tube; and a movable member, the movable member comprising: a member main portion which is inserted into the reduced-diameter portion and which presses against inner walls of the reduced-diameter portion, and an annular isolating member which fits to an outer circumferential portion of the member main portion; wherein: the movable member has a specific gravity between that of serum and that of clot, and the annular isolating member comprises at least one of a material possessing elasticity and liquid permeability, and a material possessing the quality of swelling in response to immersion in liquid.

In accordance with the apparatuses for serum separation in accordance with the second and third aspects of the present invention, it is possible to satisfactorily support the member main portion which is inserted into the blood collection tube within the cylindrical member or on the cylindrical portion, and it is possible to easily conduct the movement of the member main portion to the boundary between serum and the clot, so that it is possible to minimize the damage to the inner walls of the blood collection tube resulting from friction.

BRIEF DESCRIPTION OF THE DRAWINGS

FIG. 3A shows the state in which the serum separating device is installed in the opening of the blood collection tube.

FIG. 3B shows the state in which a blood collection pipette is inserted from above, and the collected blood is injected.

FIG. 3C shows the state in which the blood collection tube is allowed to stand and the blood is allowed to clot.

FIG. 3D shows the state in which the member main portion which supports the isolating member moves to the boundary between the serum and the clot and restrains the clot.

FIG. 3E shows the state in which the insulating member becomes tightly attached to the inner wall of the blood collection tube as a result of elasticity or swelling, and the member main portion is affixed at the boundary position.

DETAILED DESCRIPTION OF THE INVENTION

Figure 1:
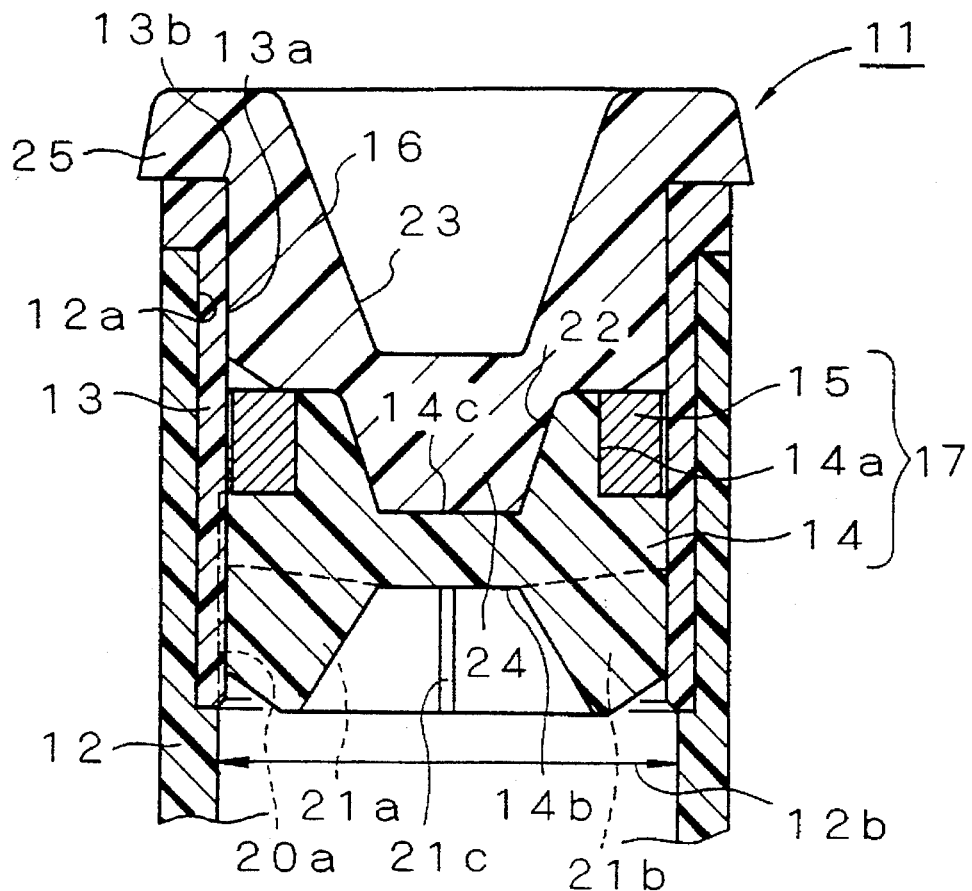
FIG. 1 is a vertical cross sectional view showing a serum separating device in accordance with a first embodiment of the present invention.

Hereinafter, various embodiments of a separating member for separation in accordance with the present invention will be discussed.

A serum separating device in accordance with the first aspect of the present invention is provided with: a cylindrical member, which fits to an opening of a blood collection tube and which has an inner diameter which is slightly smaller than an inner diameter of the opening; and a movable member, the movable member comprising: a member main portion which is inserted into the cylindrical member and which presses against inner walls of the cylindrical member, and an annular isolating member which fits to an outer circumferential portion of the member main portion; wherein the movable member has a specific gravity between that of serum and that of clot; and the annular isolating member comprises at least one of a material possessing elasticity and liquid permeability, and a material possessing the quality of swelling in response to immersion in liquid.

In a preferred embodiment, in the member main portion, a cavity portion which opens downward may be co-axially formed, and notches penetrating in a vertical direction may be formed at a portion of the member main portion which is above the cavity portion. By means of forming a cavity having such a construction and notches, the air filling the cavity portion during centrifugal separation can be rapidly vented above the member main portion from the notches, and it is possible to make smooth the mutual motion of the member main portion and the clot during centrifugal separation, so that accordingly, it is possible to weaken the shocks during centrifugal separation, and the danger of breakage in the clot and the like is eliminated.

In a preferred embodiment, the movable member has a specific gravity within a range of 1.04–1.08.

In a preferred embodiment, the isolating member comprises at least one selected from the group consisting of cellulose sponge, and swelling rubber having highly water-absorbent polymer mixed thereinto.

An apparatus for serum separation in accordance with the second aspect of the present invention is provided with: a cylindrical blood collection tube having an opening at one end thereof; a cylindrical member which fits to the opening of the blood collection tube and which has an inner diameter which is slightly smaller than the inner diameter of the opening; a movable member, the movable member comprising: a member main portion which is inserted into the cylindrical member and which presses against inner walls of the cylindrical member, and an annular isolating member which fits to an outer circumferential portion of the member main portion; wherein: the movable member has a specific gravity between that of serum and that of clot; and the isolating member comprises a material which is elastic and liquid-permeable, and/or a material which swells in response to immersion in liquid.

In a preferred embodiment, a cavity portion which is downwardly opened may be co-axially formed in the member main portion, and notches which penetrate in a vertical direction may be formed in a portion of the member main portion which is above the cavity portion. By forming a cavity portion having such a structure and notches, it is possible to rapidly dissipate the air filling the cavity portion during centrifugal separation from the notches to above the member main portion, and it is possible to make smooth the mutual motion of the member main portion and the clot during centrifugal separation, so that accordingly, it is possible to weaken shocks during centrifugal separation, and thus the danger of breakage in the clot or the like is eliminated.

In a preferred embodiment, the length of the cylindrical member in the axial direction is greater than or equal to 0.5 times the inner diameter of the blood collection tube, and less than or equal to 2 times this diameter. By means of providing the cylindrical member with such a structure, it is possible to satisfactorily support the separating member which is inserted within the cylindrical portion, and it is possible to easily and rapidly conduct movement to the boundary of the serum and the clot, so that it is possible to minimize the damage caused to the inner walls of the blood collection tube used in serum separation as a result of friction.

In a preferred embodiment, the moveable member has a specific gravity within a range of 1.04–1.08.

In a preferred embodiment, the isolating member comprises at least one selected from a group consisting of urethane foam, cellulose sponge, rubber, and swelling rubber having highly water-absorbent polymer mixed thereinto.

An apparatus for serum separation in accordance with a third aspect of the present invention is provided with: a blood collection tube, which has a structure such that a reduced-diameter portion, having an inner diameter which is less than an inner diameter of the blood collection tube at this opening; a member main portion which is inserted into this reduced-diameter portion and which presses against the inner walls of the reduced-diameter portion; and an annular isolating member which fits to the outer circumferential portion of the member main portion; a movable member which consists of the member main portion and the isolating member has a specific gravity between that of serum and that of clot, and the isolating member comprises a material which is elastic and liquid-permeable and/or a material which swells in response to liquid.

In a preferred embodiment, a cavity portion which is downwardly opened may be formed co-axially in the member main portion, and notches which penetrate in a vertical direction may be formed in a portion of the member main portion which is above the cavity portion. By forming a cavity portion having such a structure and notches, it is possible to rapidly vent the air which fills the cavity portion during centrifugal separation from the notches to above the member main portion, and it is possible to make smooth the mutual motion of the member main portion and the clot during centrifugal separation, so that accordingly, it is possible to weaken the shocks during the centrifugal separation, and the danger of breakage in the clot and the like is eliminated.

In a preferred embodiment, the length of the reduced-diameter portion in the axial direction is greater than or equal to 0.5 times the inner diameter of the blood collection tube, and less than or equal to 2 times this inner diameter. By providing the cylindrical member with such a structure, it is possible to satisfactorily support within the cylindrical portion the isolating member which is inserted, and it is possible to easily and rapidly conduct movement to the boundary between the serum and the clot, and it is thus possible to minimize the damage to the inner walls of the blood collection tube used in serum separation resulting from friction.

In a preferred embodiment, the movable member has a specific gravity within a range of 1.04–1.08.

In a preferred embodiment, the isolating member comprises at least one selected from a group consisting of urethane foam, cellulose sponge, rubber, and swelling rubber having highly water-absorbent polymer mixed thereinto.

EMBODIMENT 1

An embodiment of a serum separating device in accordance with the first aspect of the present invention will be explained.

Figure 2:
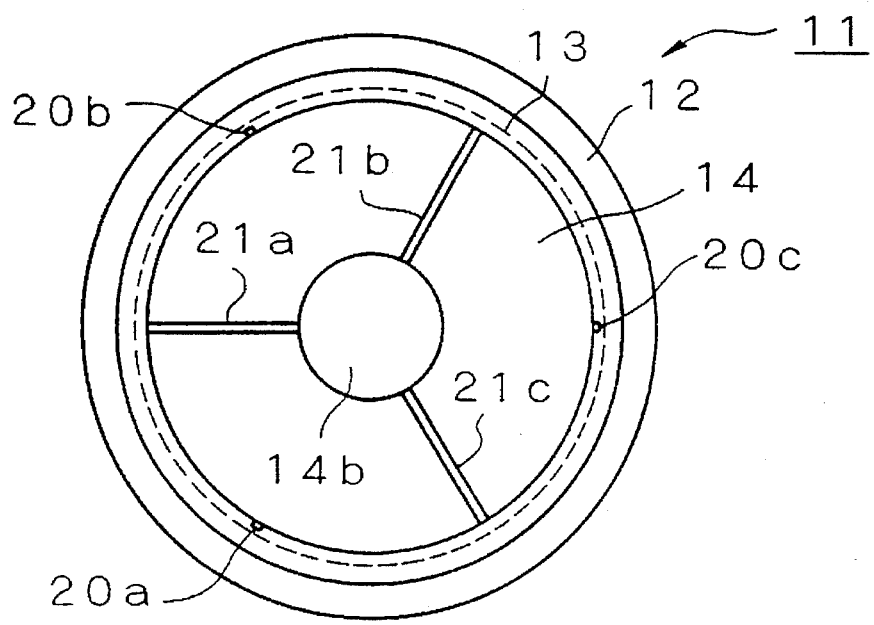
FIG. 2 is a lower surface view showing a serum separating device in accordance with the first embodiment of the present invention.

FIG. 1 is a vertical cross sectional view of a serum separating device 11, and FIG. 2 is a lower surface view of this serum separating device 11. In the Figures, reference numeral 12 indicates a blood collection tube (a cylindrical vessel) in which serum separating device 11 is installed, reference numeral 13 indicates a cylindrical member which fits to opening 12a of blood collection tube 12, reference numeral 14 indicates a member main portion which is inserted into this cylindrical member 13, reference numeral 15 indicates an annular isolating member which fits to the upper outer circumferential portion 14a of the member main portion 14, and reference numeral 16 indicates a cap which engages with member main portion 14 and cylindrical member 13.

This serum separating device 11 comprises a cylindrical member 13, a member main portion 14, and an isolating member 15.

A tube which is capable of satisfactorily maintaining a low pressure state is preferable for use as the blood collection tube 12; for example, a glass tube or a plastic tube comprising, for example, polyethylene terephthalate (PET) or the like is preferably employed.

Cylindrical member 13 has an inner diameter which is slightly smaller than the inner diameter of the opening 12a of the blood collection tube 12, for example, an inner diameter which is smaller by 0.2–3 mm, and in the inner wall thereof, a plurality of grooves 20a–20c for air escape are formed in the axial direction at three positions which possess symmetry with respect to the central axis. Hard plastics which function well as gas barriers, such as, for example, polycarbonate, or polyethylene terephthalate resin, or the like, are preferably employed as the material for this cylindrical member 13.

Here, the difference in inner diameters between the blood collection tube 12 and the cylindrical member 13 was set to a level of 0.2–3 mm; however, when the blood collection tube 12 comprises plastic, the tube is tapered, so that the lower inner diameter is smaller than the higher inner diameter, so that setting should be conducted in consideration of the inner diameter of the blood collection tube at the smallest blood amount.

Member main portion 14 has an approximate disc-shape, is flexible, and has a central portion which is made thin in the vertical direction thereof so as to easily permit the penetration of a blood collection needle; at the side of the lower surface 14b thereof, a plurality of grooves 21a–21c permitting the escape of air are formed in the direction of the outer circumferential surface from the central axis thereof at three positions possessing symmetry with respect to the central axis, and an engaging concave portion 22 having a cross sectional trapezoidal shape is formed along the central axis at the central portion of the upper surface 14c so as to engage with cap 16.

Member main portion 14 should easily permit the penetration of the blood collection needle and should possess softness and flexibility such that resealing is possible after the withdrawal of the blood collection needle. Moreover, a movable member 17 which consists of the member main portion 14 and the isolating member 15 has a specific gravity between that of serum and that of clot. Concretely, a rubber or an elastomer such that the specific gravity of the movable member 17 is within a range of 1.04–1.08, and preferably within a range of 1.045–1.055, is employed; examples thereof include, for example, styrene-butadiene rubber, butyl rubber, silicone rubber, polystyrene-type elastomer, polyamide-type elastomer, silicone-type elastomer, or the like, or, a mixture of such materials with an inorganic material such as barium sulfate or the like in order to adjust the specific gravity thereof. The hardness of such a rubber or an elastomer is within a range of 30–60 in accordance with the JISA (JISK 6301) standards.

In this case, the member main portion 14 may comprise an elastic substance having the characteristics described above; however, if, furthermore, member main portion 14 comprises a swelling rubber which is elastic and swells in response to serum, then the swelling of insulating member 15 can be made more effective, and as a result, the partitioning of the serum and the clot after centrifugal separation can be made more reliable.

Isolating member 15 comprises one or the other of a material possessing elasticity and liquid permeability, and a material which swells in response to serum, and isolating member 15 has a cross sectionally rectangular ring shape with a diameter which is slightly smaller than that of the member main portion 14, and the diameter of the hole in the central portion thereof is set so as to be slightly smaller than the outer diameter of the outer circumferential portion 14a of member main body 14.

It is preferable that this isolating member 15 not swell immediately after member main portion 14 separates from cylindrical member 13 during centrifugal separation, but rather that this member swell after reaching the boundary between the serum and the clot, so that, for example, a foaming resin such as foaming polyurethane or the like is preferably used as the material possessing elasticity and liquid permeability, and furthermore, a cellulose sponge, or swelling rubber having highly water absorbent polymers mixed thereinto are preferably employed as the materials which swell in response to serum. Furthermore, even in the case of a foaming resin or cellulose sponge which expands and swells at the moment at which binding power is lost, by carrying out a delayed foaming process, more effective use is possible.

An example of a delayed foaming processing method is a method with which a cellulose sponge in a dry state is immersed in a resin which will not affect the assayed values, for example, a hydrophobic liquid resin such as liquid silicone oil or polybutene, or a hydrophilic resin such as polyethylene glycol (PEG), polyvinyl alcohol (PVA), or the like. Furthermore, a thin coating of a hydrophilic high molecular film may be applied to the surface of the cellulose sponge.

By conducting this type of processing, it becomes possible to cause the cellulose sponge to swell at a freely selected time after it is immersed in serum. For example, when a cellulose sponge which has been immersed in 65% of the weight of the sponge of polybutene having an average molecular weight of 2400 and a viscosity of 4600 CST (centistokes) (at 98.9° C.) and has undergone delayed foaming processing is submerged in serum, the sponge will slowly begin to swell after 4 minutes.

Another advantage of impregnating with liquid resin lies in the fact that it is possible to prevent the contamination of the serum layer with blood cells from the clot layer after centrifugal separation.

Cap 16 is molded in an approximate disc shape from butyl rubber having superior gas-barrier characteristics and possessing elasticity; a concave portion 23 is formed in the upper central portion thereof so as to permit the easy penetration of a blood collection needle, and an engaging convex portion 24 having a cross sectional trapezoidal shape which engages with the engaging concave portion 22 is formed in the lower portion thereof, and an engaging portion 25 which engages with the opening 13b of the cylindrical member 13 is formed in an annular shape at the upper peripheral portion thereof.

Next, a method for the separation of the components of blood using the serum separating device 11 in accordance with the first embodiment will be explained based on FIGS. 3A–3E.

First, the serum separating device 11 is installed in opening 12a of blood collection tube 12 (FIG. 3A). In this case, it is necessary that the member main portion 14 press against the inner wall 13a of the cylindrical member 13 with a fixed pressure or more so that the member main portion 14 will not readily slide downwards from the cylindrical member 13. This blood collection tube 12 is an evacuated blood collection tube which is capable of satisfactorily maintaining a low pressure state in the interior thereof.

Next, a blood collection needle 31 is inserted into serum separating device 11 from above, and the collected blood 5 is injected (FIG. 3B). The amount of blood injected is determined in accordance with the degree of low pressure within blood collection tube 12; however, the blood is always positioned below member main portion 14, and never rises above it.

Next, this blood collection tube 12 is allowed to stand, and the blood is thus allowed to clot (FIG. 3C).

Next, centrifugal separation is conducted. Member main portion 14 slowly descends while sliding along the inner wall of cylindrical member 13, and when separation from cylindrical member 13 is achieved, isolating member 15 moves rapidly to the boundary between serum 6 and clot 7 while being satisfactorily horizontally supported in a balanced manner, and this restricts clot 7 (FIG. 3D). Until member main portion 14 separates from cylindrical member 13, the buoyancy which member main portion 14 receives from the blood is either extremely small or is nonexistent. Accordingly, for example, if the size of the centrifugal force which is applied is taken to be 1000 G, then member main portion 14 receives a force which is essentially identical to that of falling through air at 1000 G, so that it is easily possible to separate from the cylindrical member 13.

In this case, as shown in FIG. 3E, as a result of elasticity or swelling, isolating member 15 attaches tightly to the inner wall of the blood collection tube 12, and member main portion 14 is affixed at the boundary position, so as to prevent the movement of clot 7 into serum layer 6. Accordingly, as a result of this serum separating device 11, serum 6 and clot 7 are completely separated, and there is no danger that blood cells from clot 7 will contaminate serum 6. Furthermore, in the case in which the inner diameter of blood collection tube 12 varies, as well, it is possible to completely separate serum 6 from clot 7.

Hereinafter, experimental examples, which were conducted for the purpose of clarifying the effects of the serum separating device 11 in accordance with the first embodiment, will be explained.

EXPERIMENTAL EXAMPLES

First, a serum separating device 11 and a blood collection tube 12 such as those shown in FIGS. 1 and 2 were prepared.

Member main portion 14 was set at an outer diameter of 12.6 mm and a maximum height of 9 mm, and the width of grooves 21a–21c was set at 1 mm, and the central portion, which was made thin, was in a disc shape with a diameter of 4 mm and a thickness of 2 mm so as to easily permit the penetration of the blood collection needle.

This member main portion 14 is formed by the injection molding of a polystyrene-type thermoplastic elastomer (Tufftek K2141: produced by Asahi Kasei Corp., Ltd.), having a volume of 0.62 $cm^3$ and a specific gravity of 1.0, in the shape described above.

Furthermore, the isolating member 15 is formed by stamping a ring having an outer diameter of 12.3 mm, an inner diameter of 8.5 mm, and a thickness of 3 mm from a sheet-form rubber compound having a specific gravity of 1.23 and having mixed thereinto a highly water-absorbent resin (Sumika gel: produced by Sumitomo Kagaku Corp., Ltd.).

When this member main portion 14 and isolating member 15 were combined, the actual specific gravity was 1.053.

Furthermore, the cylindrical member 13 has an outer diameter of 14.2 mm, an inner diameter of 12.6 mm, and a height of 15 mm, and is formed by the injection molding of a polyethylene terephthalate resin so that the upper end thereof has a flange shape.

Furthermore, cap 16 is formed from butyl rubber possessing satisfactory air-tightness.

Furthermore, blood collection tube 12 is formed by the injection molding of polyethylene terephthalate (PET) in a shape such that the effective volume thereof is 10 ml, the height is 100 mm, and the inner diameter of the opening 12b at the upper end thereof is 13.2 mm, the outer diameter thereof is 15.6 mm, and the inner diameter of the lower end thereof is 12.8 mm. Subsequently, serum separating device 11 fitted to blood collection tube 12, and an evacuated blood collection tube having an evacuated degree of 450 mmHg was formed.

Next, approximately 5 ml of blood was injected into this blood collection tube 12. In this case, member main portion 14 was strongly attached to cylindrical member 13, so that there was no danger of the separation of member main portion 14 from cylindrical member 13. Next, this blood collection tube was allowed to stand for 6 hours and the blood was allowed to clot, and subsequently, centrifugal separation was conducted at 1000 G for a period of 10 minutes. After centrifugal separation, member main body 14 was positioned at the boundary surface between serum 6 and clot 7, and was in such a state that it was on top of clot 7. In this case, isolating member 15 adhered completely to the inner wall of the blood collection tube 12, so that the serum 6 and the clot 7 were completely separated, and even if the blood collection tube 12 was agitated, there would be no mixing of serum 6 and clot 7, and neither would there be any hemolysis of the blood cells.

When the blood collection tube 12 was stored for a period of 1 month at a low temperature of approximately 5° C., hemolysis of the blood cells in clot 7 occurred; however, there was no mixture of the hemolyzed blood with the serum 6.

Here, cylindrical member 13, member main portion 14, isolating member 15, and cap 16 comprise high molecular materials which are inert with respect to blood, so that even in the case of storage for a long period of time, there would be no effect occurring between the components of the serum and the members such as adsorption, leaching, or the like, so that a highly accurate diagnostic test is possible.

In FIGS. 1 and 2, an example of the serum separating device in accordance with the present invention was depicted in which the isolating member fitted to the upper portion of the member main portion; however, the position of the isolating member is not necessarily so limited, and it may be in the central portion of the outer circumferential surface of the member main portion, or may fit to the lower portion of the member main portion.

In the same manner, in FIGS. 1 and 2, an example was shown in which the engaging concave portion was formed in the upper surface of the member main portion; however, the shape of the member main portion is not necessarily so limited, and a conical angled surface may be formed in the upper portion of the member main portion, or the upper portion of the member main portion may comprise a flat surface.

EMBODIMENT 2

Figure 4:
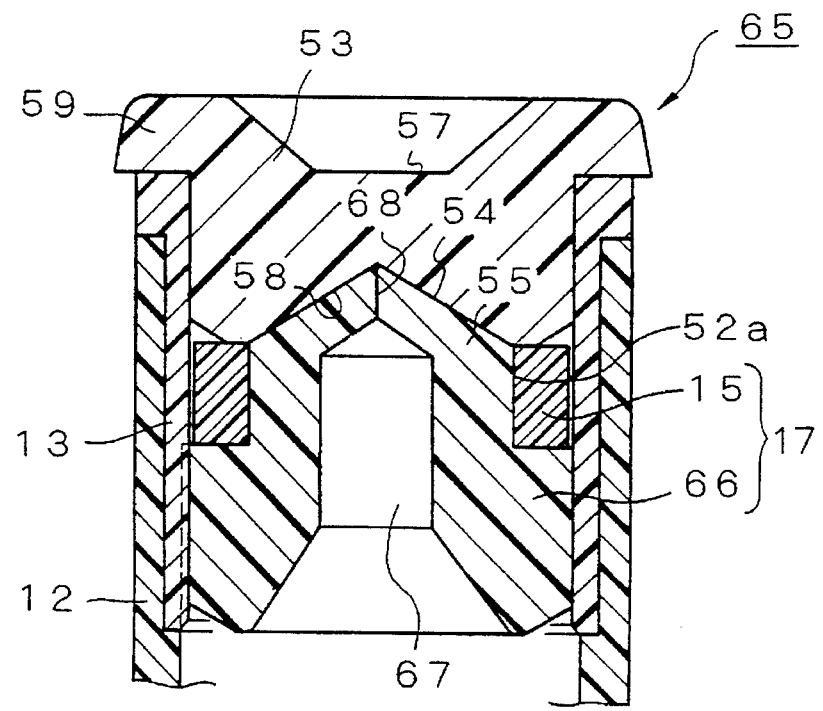
FIG. 4 is a vertical cross sectional view showing a serum separating device in accordance with the second embodiment of the present invention.

FIG. 4 is a vertical cross sectional view of a serum separating device 65 in accordance with a second embodiment.

In FIG. 4, structural elements which are identical to those of the serum separating device of FIG. 1 are given identical reference numbers, and an explanation thereof will be omitted here.

In the central portion of the member main portion 66 of this serum separating device 65, a cavity portion 67, which is opened toward the downward side thereof and which supports air, is formed co-axially, and notches 68 which penetrate in a vertical direction are formed in the central portion of this member main portion 66 above the cavity portion 67.

Figure 5:
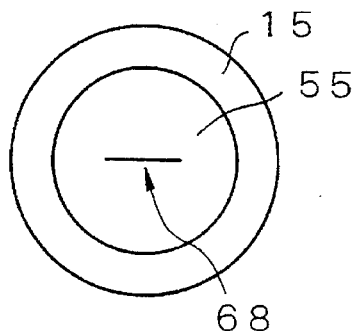
FIG. 5 is a top view showing a first example of the notches of a serum separating device in accordance with the second embodiment of the present invention.
Figure 6:
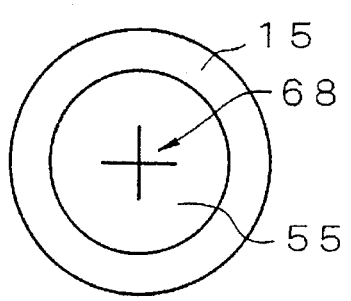
FIG. 6 is a top view showing the second example of the notches of a serum separating device in accordance with a second embodiment of the present invention.
Figure 7:
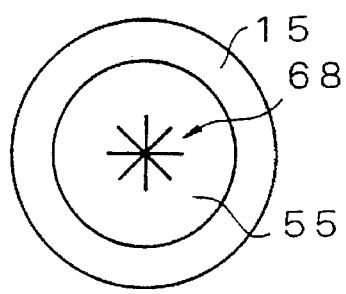
FIG. 7 is a top view showing a third example of the notches of a serum separating device in accordance with the second embodiment of the present invention.

These notches 68 are not openings such as penetrating holes, but rather are notched by means of an edged tool such as a carving blade or the like, and are normally in a closed state; however, when a load is placed thereon, such as during centrifugal separation, they open slightly. FIGS. 5, 6, and 7 show concrete examples of the shape of these notches 68; a number of shapes may be employed, such as a single notch (FIG. 5), a cross-shaped notch (FIG. 6), a double cross-shaped notch (FIG. 7), or the like.

In the case, for example, of a single notch, in the case in which the member main portion 66 comprises a molded body comprising an elastic material such as rubber or an elastomer having a hardness within a range of approximately 40–60 in accordance with the JISA (JISK 6301) Standards, and the thickness of the engaging convex portion 55 is within a range of 0.5–2 mm, then the size of the notch 68 should preferably be approximately 5 mm.

Furthermore, a movable member 17 which consists of the member main portion 66 and the isolating member 15 should have a specific gravity appropriately between that of serum and that of clot, and more specifically, should be within a range of 1.04–1.08, and preferably within a range of 1.045–1.055.

In this serum separating device 65, in member main portion 66, a cavity portion 67 which opens downwards is co-axially formed, and notches 68 are formed in the center of the engaging convex portion 55 of member main portion 66 above cavity portion 67, and thereby, in the case in which collected blood is placed in the blood collection tube 12, centrifugal force does not act, so that the cavity portion 67 becomes full of air, and furthermore, neither serum nor clot passes, so that accordingly, diagnostic blood test is unaffected. Here, when a centrifugal force on the level of 1000 G is applied, the serum separating device 65 begins to descend; however, during this descent, gravity acts on member main portion 66, and furthermore, the buoyancy of the air simultaneously acts on cavity portion 67, and the angled surface 54 of the member main portion 66 bends slightly upward, and thereby, notches 68 open slightly, and the air filling cavity portion 67 passes through notches 68, and is vented above member main portion 66. After the venting of the air, the bending of angled surface 54 is eliminated, so that the notches 68 close, and during this period, member main portion 66 moves to the boundary between serum and the clot as a result of centrifugal force, and is stopped.

In this case, the air within cavity portion 67 acts as a cushion, so that the movement of the member main portion 66 and the clot with respect to one another is made smooth. Accordingly, shocks are lessened, and there is no danger of hemolysis resulting from breakage of the clot.

As explained above, in accordance with this serum separating device 65, in member main portion 66, a cavity portion 67 which opens downwardly is formed in a coaxial manner, and notches 68 which penetrate in a vertical direction are formed in the central portion of the member main portion 66 above the cavity portion 67, so that it is possible to make smooth the movement of the member main portion 66 and the clot with respect to one another, and accordingly, it is possible to lessen shocks, and to prevent hemolysis resulting from breakage of the clot.

In this serum separating device 65, it is possible to set the centrifugal force at which air will be vented from the cavity portion 67 by means of the size and the shape of the notches 68. By means of this, it is possible to cause the air within cavity portion 67 to be vented and the member main portion 66 to descend after the serum and the clot have been separated to a certain degree after the initiation of centrifugal separation, and thus to minimize the deposition of a trace amount of clot on member main portion 66.

In this serum separating device 65, a conical angled surface 54 is formed on the upper portion of the member main portion 66; however, the upper portion of member main portion 66 may also comprise a flat surface.

Furthermore, in the serum separating devices in accordance with Embodiments 1 and 2, in addition to a prior insertion method, that is to say, a method in which the member is installed in advance in the blood collection tube, as in, for example, an evacuated blood collection tube, a post-insertion method, that is to say, one in which blood is injected into the blood collection tube and allowed to clot, and then the member is inserted, and centrifugal separation carried out, may also be preferably employed.

EMBODIMENT 3

In the apparatus for serum separation in accordance with the second aspect of the present invention, a cylindrical blood collection tube having an opening at one end thereof, a cylindrical member which fits to the opening of the blood collection tube and has an inner diameter which is slightly smaller than the inner diameter of the opening, a member main portion which is inserted into the cylindrical member and which presses against the inner walls of the cylindrical member, and an annular isolating member which fits to the outer circumferential portion of the member main portion, a movable member which consists of the member main portion and the isolating member has a specific gravity between that of serum and that of clot, are provided, and the isolating member comprises a material which is elastic and liquid-permeable, and/or a material which swells in response to immersion in liquid. That is to say, a serum separating device in accordance with the first aspect of the present invention fits to the opening of a cylindrical blood collection tube possessing an opening at one end thereof.

The apparatus for serum separation in accordance with the third aspect of the present invention is provided with: a blood collection tube in which a cylindrical portion having an inner diameter which is slightly smaller than the inner diameter of an opening of a cylindrical vessel is formed in that opening; a member main portion which is inserted into the cylindrical portion and which presses against the inner walls of the cylindrical member; and an isolating member which fits to the outer circumferential portion of the member main portion, a movable member which consists of the member main portion and the isolating member has a specific gravity between that of serum and that of clot; are provided, and the isolating member comprises a material possessing elasticity and liquid permeability and/or a material which expands in response to immersion in liquid. That is to say, the member main portion and the isolating member, which comprise the primary structural elements of the present invention, are inserted in a blood collection tube formed with a reduced-diameter portion having a reduced inner diameter at an opening of the blood collection tube; the structure is such that the blood collection tube and the cylindrical member in the apparatus for serum separation in accordance with the second aspect of the present invention are made unitary.

Figure 8:
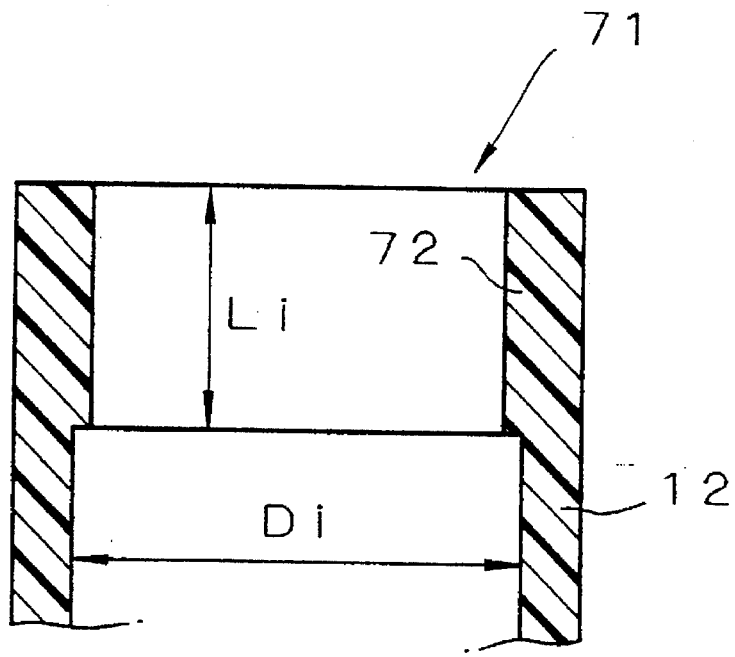
FIG. 8 is vertical cross sectional view showing an example of a blood collection tube in an apparatus for serum separation in accordance with a third aspect of the present invention.
Figure 9:
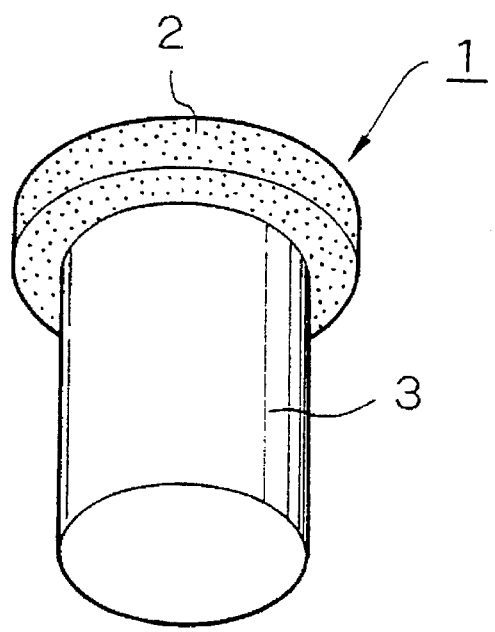
FIG. 9 is an angled view showing a conventional serum filtering piston.
Figure 10:
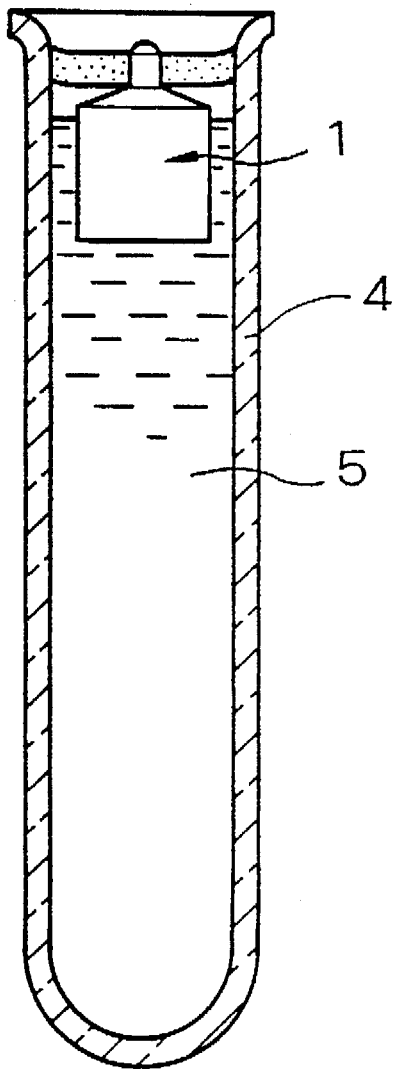
FIG. 10 is a process diagram showing the centrifugal separation operation of blood by means of this conventional serum filtering piston.
Figure 11:
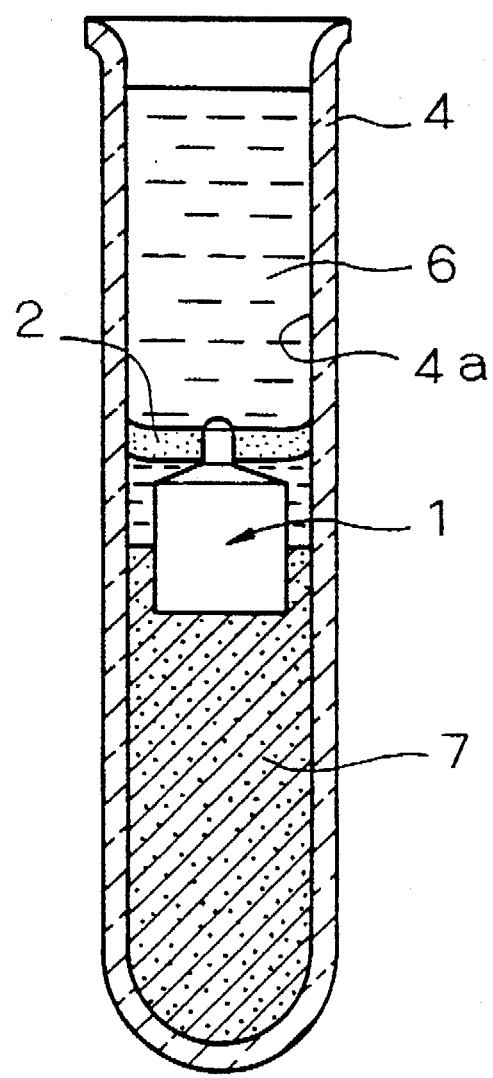
FIG. 11 is a process diagram showing the centrifugal separation operation of blood by means of this conventional serum filtering piston.

In FIG. 8, an embodiment of the blood collection tube, which is a structural element in the apparatus for serum separation in accordance with the third aspect of the present invention, is shown.

This blood collecting tube of the apparatus for serum separation 71 is an evacuated blood collection tube in which a low pressure state can be satisfactorily maintained; a reduced-diameter portion having a reduced diameter is formed at an opening of the blood collection tube. In a preferable embodiment, the length Li in the axial direction of the reduced-diameter portion 72 is greater than or equal to 0.5 times that of the inner diameter Di of main portion of the vessel, and is equal to or less than 2 times this diameter. The reduced-diameter portion having this structure is capable of satisfactorily supporting the separating member which is inserted within the cylindrical portion 72, and it is possible to easily and rapidly conduct the movement thereof to the boundary between the serum and the clot, and it is possible to limit the damage caused to the inner wall of the blood collection tube 71 for use in serum separation resulting from friction.

In the same way, in a preferable embodiment, in the second aspect, the length Li in the axial direction of the cylindrical member is greater than or equal to 0.5 times the inner diameter Di of the main portion of the vessel, and is less than or equal to 2 times this diameter. The cylindrical member having such a structure is capable of satisfactorily supporting the separating member which is inserted within the cylindrical portion 72, and it is possible to easily and rapidly conduct the movement thereof to the boundary of the serum and the clot, and it is possible to reduce damage caused to the inner walls of the blood collection tube 71 for serum separation resulting from friction.

It will be appreciated by those skilled in the art that numerous variations and modifications may be made to the invention as shown in the specific embodiments without departing from the spirit or scope of the invention as broadly described. The present embodiments are therefore to be considered in all respects as illustrative and not restrictive.

What is claimed is:

1. A serum separating device for separating the serum and the clot of blood by centrifugal separation, and serum separating device comprising:

a cylindrical member, which fits to an opening of a blood collection tube and which has an inner diameter which is slightly smaller than an inner diameter of said opening, and a movable member, said movable member comprising;
   a member main portion which is inserted into said cylindrical member and which presses; against inner walls of said cylindrical member, and
   an annular isolating member which is annular-shaped and fits to an outer circumferential portion of said member main portion;

wherein;

said movable member has a specific gravity between that of serum and that of clot; and said annular isolating member comprises:
   a material possessing elasticity, liquid permeability, and the quality swelling in response to immersion in liquid.

2. A serum separating device in accordance with claim 1, wherein said member main portion has a cavity portion formed coaxially on the bottom side of said member main portion, and notches which penetrate in a vertical direction are formed in a portion of said member main portion above said cavity portion.

3. A serum separating device in accordance with claim 1, wherein:

said movable member has a specific gravity within a range of 1.04–1.08.

4. A serum separating device in accordance with claim 1, wherein:

said annular isolating member comprises at least one of cellulose sponge and swelling rubber having a highly water-absorbent polymer mixed thereinto.

5. A serum separating device in accordance with claim 1, wherein:

said annular isolating member comprises a material treated with a delayed foaming process.

6. A serum separating device in accordance with claim 5, wherein:

said delayed foaming process comprises immersion of a dry cellulose sponge in a resin.

7. A serum separating device in accordance with claim 1, wherein:

said member main portion comprises a welling rubber which is elastic and swells in response to serum.

8. An apparatus for use in serum separation for separating blood into serum and clot by means by centrifugal separation, said apparatus comprising:

a cylindrical blood collection tube having an opening at one end thereof;

a cylindrical member, which fits to an opening of said blood collection tube and which has an inner diameter which is slightly smaller than an inner diameter of said opening; and a movable member, said movable member comprising:

a member main portion which is inserted into said cylindrical member and which presses against inner walls of said cylindrical member, and an annular isolating member which is annular-shaped and fits to an outer circumferential portion of said member main portion;

wherein:

said movable member has a specific gravity between that of serum and that of clot; and said annular isolating member comprises:

a material possessing elasticity, liquid permeability, and the quality of swelling in response to immersion in liquid.

9. An apparatus for serum separation in accordance with claim 8, wherein:

said member main portion has cavity portion formed coaxially on the bottom side of said member main portion; and notches which penetrate in a vertical direction are formed in a portion of said member main portion above said cavity portion.

10. An apparatus for serum separation in accordance with claim 8, wherein:

a length in the axial direction of said cylindrical member is not less than 0.5 times the inner diameter of said blood collection tube, and is not more than 2 times the inner diameter of said blood collection tube.

11. An apparatus for serum separation in accordance with claim 8, wherein:

said movable member has a specific gravity within a range of 1.04–1.08.

12. An apparatus for serum separation in accordance with claim 8, wherein:

said annular isolating member comprises at least one of cellulose sponge rubber and swelling rubber having a highly water absorbent polymer mixed thereinto.

13. A serum separating device in accordance with claim 8, wherein:

said annular isolating member comprises a material treated with a delayed foaming process.

14. An apparatus for serum separation in accordance with claim 13, wherein:

said delayed foaming precess comprises immersion of a dry cellulose sponge in a resin.

15. An apparatus for serum separation in accordance with claim 8, wherein:

said member main portion comprises a welling rubber which is elastic and swells in response to serum.

16. An apparatus for use in serum separation for separating blood into serum and clot by means of centrifugal separation, said apparatus comprising:

a blood collection tube formed with a reduced-diameter portion having a reduced inner diameter at an opening of the blood collection tube; and a movable member, said movable member comprising:

a member main portion which is inserted into said reduced-diameter portion and which presses against inner walls of said reduced-diameter portion, and an annular isolating member which is annular-shaped and fits to an outer circumferential portion of said member main portion;

wherein: said movable member has a specific gravity between that of serum and that of clot, and said annular isolating member comprises:

a material possessing elasticity, liquid permeability, and the quality of swelling in response to immersion in liquid.

17. An apparatus for use in serum separation in accordance with claim 16, wherein:

said member main portion has a cavity portion formed coaxially on the bottom said of said member main portion; and notches which penetrate in a vertical direction are formed in a portion of said member main portion above said cavity portion.

18. An apparatus for serum separation in accordance with claim 16, wherein:

the length in the axial direction of said reduced-diameter portion is not less than 0.5 times the inner diameter of said blood collection tube, and is not more than 2 times the inner diameter of said blood collection tube.

19. An apparatus for serum separation in accordance with claim 16, wherein:

said movable member has a specific gravity within a range of 1.04–1.08.

20. An apparatus for serum separation in accordance with claim 16, wherein:

said annular isolating member comprises at least one of cellulose sponge and swelling rubber having a highly water absorbent polymer mixed thereinto.

21. An apparatus for serum separation in accordance with claim 16, wherein:

said annular isolating member comprises a material treated with a delayed foaming process.

22. An apparatus for serum separation in accordance with claim 21, wherein:

said delayed foaming precess comprises immersion of a dry cellulose sponge in a resin.

23. An apparatus for serum separation in accordance with claim 21, wherein:

said member main portion comprises a welling rubber which is elastic and swells in response to serum.

* * * * *

UNITED STATES PATENT AND TRADEMARK OFFICE
CERTIFICATE OF CORRECTION

PATENT NO. : 5,632,895
DATED : May 27, 1997
INVENTOR(S) : Tsukagoshi et al.

It is certified that error appears in the above-indentified patent and that said Letters Patent is hereby corrected as shown below:

Column 8, Line 6,      now reads "a range of 1.045-1,055", should read --a range of 1.045-1.055--.

Column 16, Line 20,      now reads "bottom said of said", should read --bottom side of said--.

Column 16, Line 46,      now reads "foaming precess", should read --foaming process--.

Signed and Sealed this

Twenty-fifth Day of November, 1997

*Attest:*

BRUCE LEHMAN

*Attesting Officer*      *Commissioner of Patents and Trademarks*